United States Patent [19]

Oakley et al.

[11] Patent Number: 5,413,107

[45] Date of Patent: May 9, 1995

[54] ULTRASONIC PROBE HAVING ARTICULATED STRUCTURE AND ROTATABLE TRANSDUCER HEAD

[75] Inventors: Clyde G. Oakley; Joseph V. Ranalletta, both of Englewood; Stephen J. Douglas, Parker; Wing K. Law, Denver, all of Colo.

[73] Assignee: Tetrad Corporation, Englewood, Colo.

[21] Appl. No.: 197,327

[22] Filed: Feb. 16, 1994

[51] Int. Cl.⁶ ............................................. A61B 8/12
[52] U.S. Cl. ....................................... 128/662.06
[58] Field of Search ............... 128/660.10, 662.03, 128/662.06; 601/2; 73/621, 633

[56] References Cited

U.S. PATENT DOCUMENTS

| | | |
|---|---|---|
| 3,557,780 | 1/1971 | Sato . |
| 4,462,408 | 7/1984 | Silverstein et al. . |
| 4,489,727 | 12/1984 | Matsuo et al. . |
| 4,566,620 | 1/1986 | Green et al. . |
| 4,582,067 | 4/1986 | Silverstein et al. . |
| 4,688,554 | 8/1987 | Habib . |
| 4,696,544 | 9/1987 | Costella . |
| 4,728,020 | 3/1988 | Green et al. . |
| 4,756,313 | 7/1988 | Terwilliger . |
| 4,757,818 | 7/1988 | Angelsen . |
| 4,771,788 | 9/1988 | Millar . |
| 4,834,102 | 5/1989 | Schwarzchild et al. . |
| 4,869,263 | 9/1989 | Segal et al. . |
| 4,895,158 | 1/1990 | Kawabuchi et al. ............ 128/662.06 |
| 4,977,898 | 12/1990 | Schwarzschild et al. . |
| 5,050,610 | 9/1991 | Oaks et al. . |
| 5,090,414 | 2/1992 | Takano ............................ 128/662.06 |
| 5,099,850 | 3/1992 | Matsui et al. . |
| 5,105,819 | 4/1992 | Wollschlager et al. . |
| 5,158,086 | 10/1992 | Brown et al. . |
| 5,170,787 | 12/1992 | Lindegren . |
| 5,170,793 | 12/1992 | Takano et al. . |
| 5,176,142 | 1/1993 | Mason . |
| 5,181,514 | 1/1993 | Solomon et al. . |
| 5,191,890 | 3/1993 | Hileman . |
| 5,199,437 | 4/1993 | Langberg . |
| 5,207,225 | 5/1993 | Oaks et al. . |
| 5,215,092 | 6/1993 | Wray . |
| 5,219,111 | 6/1993 | Bilotti et al. . |
| 5,254,130 | 10/1993 | Poncet et al. . |
| 5,255,684 | 10/1993 | Rello ............................... 128/662.06 |

*Primary Examiner*—George Manuel
*Attorney, Agent, or Firm*—Michael M. de Angeli

[57] ABSTRACT

An articulated ultrasonic probe for endoscopic examination comprises a transducer head, for example, having one or more rows of independently actuable transducer elements extending along the surface of the probe, parallel to the axis thereof. The probe comprises an articulable section while the transducer head is journaled for rotation with respect to the tip of the probe. In use the tip of the probe is juxtaposed to a structure to be examined; the articulated section of the probe and the rotation of the transducer are controlled separately, such that the transducer elements can be juxtaposed to the structure to be examined. A series of angularly-spaced images may be formed by rotation of the transducer about its axis after articulation of the probe.

20 Claims, 7 Drawing Sheets

ULTRASONIC PROBE HAVING ARTICULATED STRUCTURE AND ROTATABLE TRANSDUCER HEAD

FIELD OF THE INVENTION

This invention relates to an improved articulated ultrasonic probe for endoscopic imaging of a body part, and to improved imaging methods enabled thereby.

BACKGROUND OF THE INVENTION

It is relatively common to perform ultrasonic examination of body parts of patients. Ultrasonic examinations are, of course, commonly carried out using an external ultrasonic probe in contact with the body part to be examined, that is, external to the body. The present invention is directed more particularly to endoscopic ultrasonic examination. As used herein, "endoscopic" ultrasonic examination refers to examination performed using a ultrasonic probe inserted through a portal in the patient's body, either a naturally occurring portal, such as the esophagus or rectum, or a surgically-formed portal.

In endoscopic ultrasonic imaging processes, a probe comprising a transducer head is inserted through an appropriate portal and manipulated so that the transducer head contacts the body part to be examined. The ultrasonic transducer is then energized by high-frequency signals passed to the transducer head via electrical conductors running down the length of the probe, such that pulses of ultrasonic energy are transmitted into the body part to be examined. The ultrasonic energy is reflected differentially from structures within the body part to be examined. The reflected energy is detected, typically by the same transducer, which then provides an electrical signal responsive to detection of the reflected energy. These signals can be processed according to generally known techniques to yield images of the body part to be examined.

It will be apparent that the transducer head must be properly aligned with respect to the body part to be imaged in order that a useful image can be formed. The prior art shows many structures for thus juxtaposing transducers of ultrasonic probes to body structures to be examined, and also shows various types of transducers and transducer head assemblies, including single-element and multiple-element transducer heads. The elements of multiple-element transducer heads are typically separately excitable in order to transmit ultrasonic energy in a specific pattern, and are operated so as to separately detect reflected energy.

Probes that are controllably articulable in specific bending planes in order to dispose the transducer head in a particular orientation with respect to a structure to be imaged are shown in a number of patents. For example, U.S. Pat. Nos. 5,170,787 to Lindegren, 5,158,086 to Brown et al, and 5,105,819 to Wollschläger et al disclose specific structures for articulated probes. The probe structures shown by these patents typically comprise a series of "vertebrae" extending along the length of an articulable portion of the probe. The vertebrae are pivotally joined to one another, such that their peripheries can be brought toward one another along a line extending along the outer edge of the articulable portion of the probe, while being spaced farther from one another along a diametrically opposed line. In this case, the probe bends in a plane including the two lines. Typically, the articulated section of the probe is operated by flexible tension members running parallel to the diametrically opposed lines, and controlled by a push-pull control arrangement, so as to simultaneously exert tension on one tension member, and release tension on the other. Hand-grippable knobs may be provided to allow a user to exert tension on one of the tension members while correspondingly releasing tension on the other. Such a structure, as used for an optical endoscope, is shown in U.S. Pat. No. 3,557,780 to Sato.

Articulable probe structures comprising vertebrae pivoted alternatingly to one another about orthogonal pivot axes are also known, for separately controllable articulation in orthogonal planes. In this case, two pairs of tension members and two push-pull control arrangements are provided, so as to provide separate articulation. Commonly, the push-pull control arrangements for such "four-way" articulated probes are operated by coaxial hand-grippable knobs; see U.S. Pat. Nos. 5,050,610 and 5,207,225 to Oaks et al.

In the Brown et al patent, generally cruciform vertebrae are joined by ball and socket snap-fit elements on the probe's axis, while four tension members are maintained at radially outward, circumferentially equally spaced positions by bearings formed on the cruciform portions of the vertebrae. Flexible electrical conductors communicating excitation signals to the ultrasonic transducer head and returning detected signals responsive to the detected ultrasonic energy are disposed between the cruciform portions of each of the vertebrae. The Brown et al patent further discloses motor-driven control of the tension members, such that rather than rotate a hand-grippable knob operating a push-pull mechanism to exert tension on one tension member of each pair while releasing tension on the other, the operator simply presses a button accomplishing the same end through the intermediary of an electric motor.

As indicated above, a number of different transducer head designs are shown in the prior art, providing a number of different ultrasonic energy emission patterns. Commonly, the transducer is "end firing"; that is, the transducer emits ultrasonic energy essentially from the end of the probe, such that the axis of the center of the probe is normally perpendicular to the structure of interest. Other references show transducers for performing a circular scan centered on the axis of elongation of the probe. See, for example, Matsui et al U.S. Pat. No. 5,099,850, disclosing a transducer rotated about the axis of the probe tip by a motor located in a handpiece and driving the transducer by a flexible cable extending along a lumen of the probe.

The prior art also shows further types of ultrasonic transducers and further transducer positioning arrangements. For example, U.S. Pat. Nos. 5,191,890 to Hileman and 5,215,092 to Wray appear to relate to the same system, and show a side-firing ultrasonic transducer mounted at the tip of an articulable section of the probe. See, e.g., FIGS. 3–5 of the Hileman patent.

Also of interest is U.S. Pat. No. 4,756,313 to Terwilliger showing a side-firing transducer separately pivotable about two orthogonal axes, both perpendicular to the axis of elongation of a rigid probe, so that a "fan-shaped" scan pattern can be oriented in various positions with respect to a structure to be imaged.

U.S. Pat. No. 5,199,437 to Langberg teaches a transducer having a helical scan pattern, this being stated to improve the image processing capabilities.

U.S. Pat. Nos. 4,834,102 and 4,977,898 to Schwarzchild et al show a miniature encapsulated ultrasonic transducer, having a scanning mechanism including a motor disposed in the tip of an ultrasonic transducer head.

U.S. Pat. Nos. 5,181,514 to Solomon et al and 5,176,142 to Mason relate to a system wherein a transducer array disposed at the end of a probe is rotated about an axis perpendicular to the axis of elongation of the probe by a motor located at a proximal end of the probe, so as to allow controllable alignment of the scanning plane. A position feedback device provides a signal indicative of the position of the transducer for analysis of the reflected ultrasonic energy in generation of an image.

A number of patents, including U.S. Pat. Nos. 4,869,263 to Segal et al, 4,771,788 to Millar, 4,757,818 to Angelsen, and 4,582,067 to Silverstein et al show Doppler blood flow sensors for disposition at the end of a probe. The Silverstein et al patent combines this with an articulable endoscope for providing a visible image of a body part. U.S. Pat. No. 4,462,408, also to Silverstein et al, teaches a flexible endoscope providing both visible and ultrasonic imaging capabilities.

U.S. Pat. No. 5,170,793 to Takano et al shows an ultrasonic probe wherein a mirror inclined at 45 degrees to the axis of elongation of the probe is continuously rotated by a flexible cable connected to a motor. The mirror is disposed opposite an ultrasonic transducer, such that as the mirror rotates a circular scan is effected. U.S. Pat. No. 4,489,727 to Matsuo et al shows a similar structure in an articulated probe.

The Oaks et al U.S. Pat. Nos. 5,207,225 and 5,050,610 teach an ultrasonic scan head for transesophageal use wherein a side-firing transducer emitting a "fan-shaped" beam can be rotated about an axis transverse to the tip of the probe. Compare FIGS. 2A and 2B of the Oaks et al '225 patent. The Oaks et al patents also teach, as mentioned above, that the probe can be separately articulated in orthogonal planes by operation of co-axial control knobs. The axis about which the transducer of Oaks et al rotates is fixed with respect to the planes of articulation of the probe. Assuming access is possible, such "four-way" articulation, together with the capability of rotating the entire probe about its axis of elongation, is sufficient to allow the side-firing transducer of Oaks to be juxtaposed to all sides of structures to be imaged. However, given that standard surgical procedures dictate use of certain portals only, it can be difficult using the Oaks et al and other known probes to form desired images of numerous body structures of interest. Moreover, having achieved a desired relation between the Oaks et al probe and the structure of interest, it is in many circumstances difficult to move the transducer head to another desired position.

More particularly, using a probe with a side-firing transducer array, that is, having an array of individual transducer elements extending along a line on the outer surface of the probe and parallel to its axis of elongation, it is difficult to mimic the scanning movements a physician uses when the probe is held in his or her hand, e.g., for external ultrasonic examination. It would be desirable to allow physicians to use the same motions for external and endoscopic examinations, as this would assist them in interpreting the images formed.

Physicians often use an external ultrasonic imaging technique wherein the image plane is perpendicular to the tissue surface, that is, extends into the body structure to be examined, while the probe is systematically moved over the surface, the probe motion being perpendicular to the scan plane. For example, a side-firing transducer may be moved along the abdomen of a pregnant woman, emitting a fan-shaped beam perpendicularly into the abdominal cavity. As the transducer is moved slowly perpendicular to the scan plane, a sequence of cross-sectional images is displayed.

A surgeon using a side-firing linear array transducer together with a four-way articulating probe might desire to make a similar sequence of images of the liver, that is, to see a sequence of cross-sectional images perpendicular to the surface of the organ. The surgeon may typically start by manipulating the probe such that the image plane is perpendicular to the plane of articulation, so that he can image perpendicularly to the tissue when the contact point is far removed from the portal. If he moves in a direction perpendicular to the image plane, that is, by articulating the probe, the probe end ultimately comes into contact with the tissue beneath the portal. If he has not readjusted the probe, the transducer will be firing parallel to the tissue and will not obtain an image. Accordingly, in order to obtain the proper orientation, the surgeon is required to change the plane of the articulation, e.g., by simultaneously operating two push-pull control arrangements, while also rotating the probe 90 degrees about its axis. Thus, the surgeon must simultaneously adjust three parameters to mimic a simple hand-held scan, and must do so without being able to observe the motion of the tip of the probe. This requires substantial coordination and is difficult for many practitioners to perform effectively.

Furthermore, the degree of linear movement provided is often limited. For example, a surgeon imaging the common bile duct using laparoscopic ultrasonic techniques eventually reaches a location where the transducer cannot be inserted any further. If the surgeon is using a rigid side-firing probe, he or she may then rotate the probe about its axis to obtain a series of angularly-spaced images, including structures somewhat beyond the point of linear motion. If the surgical portal does not allow placement of a straight probe into the appropriate spot for imaging the structure of interest, the surgeon must use an articulated probe to obtain the proper placement. However, using a conventional articulated probe precludes rotation of the probe to obtain angularly-spaced images, as above.

It can therefore be seen that despite the existence of substantial prior art directed to ultrasonic imaging probes, including probes which are articulable in one or two planes, and probes which include transducers rotatable about various axes to alter the scan orientation, there remain substantial deficiencies in the prior art.

The prior art also includes U.S. Pat. No. 4,696,544 to Costella, disclosing an articulable fiber optic device for optical inspection of the interiors of jet engine parts and the like. U.S. Pat. No. 4,688,554 to Habib shows a fiber-optic optical imaging endoscope slidably disposed within an articulated sleeve, in one embodiment including a bellows in the articulated section thereof. The endoscope forms an image directly opposite its tip. The sleeve is articulated to be bendable in a single direction. Thus, in order to juxtapose the imaging tip to a structure of interest, the sleeve is rotated to a desired angular position, defining a desired bending plane, and is then articulated. See Habib at col. 5, lines 52–63.

The prior art also includes a number of instruments for purposes other than ultrasonic imaging, wherein a variety of different motions are provided for implements at the tips of probes. For example, U.S. Pat. No. 5,254,130 to Poncet et al shows a surgical device wherein a cutting implement is disposed for rotation at the tip of a probe flexing responsive to a change in temperature of a shape memory element. U.S. Pat. No. 5,219,111 to Bilotti et al shows a surgical stapler comprising a stapling mechanism mounted on the end of an elongated shaft, the shaft being rotatable about its axis with respect to an actuating handle, and the stapling mechanism being pivotable about an axis normal to the shaft. See Col. 3, lines 19–24. A similar device is shown in U. S. Pat. No. 4,728,020 to Green et al. See also U.S. Pat. No. 4,566,620, also to Green et al, and showing further positional possibilities for a surgical stapler.

OBJECTS OF THE INVENTION

It is therefore an object of the invention to provide an improved endoscopic ultrasonic imaging probe providing substantially increased flexibility in imaging techniques as compared to probes in the prior art.

It is a further object of the invention to provide improved, more flexible methods of imaging the body structures of patients.

SUMMARY OF THE INVENTION

These and other objects of the invention which will appear as the discussion below proceeds are satisfied by the present invention, whereby a probe articulable in at least one plane comprises a transducer head controllably rotatable about the axis of the tip of the probe, that is, with respect to the plane of articulation. Accordingly, after the probe has been inserted into a surgical portal, it can be articulated to dispose the probe head in juxtaposition to the body structure to be examined. The transducer can then be rotated about the axis of the tip of the probe, for example, to obtain a variety of angularly-spaced images. The transducer head may assume any of a number of configurations; for example, the transducer may comprise an elongated array of independently actuable transducer elements in at least one row extending longitudinally along the probe head.

More generally, the endoscope according to the invention provides a second degree of freedom in imaging techniques, in that the transducer head can be rotated about its own axis, that is, about the axis of the tip of the probe, while the axis of the tip of the probe can be articulated with respect to the principal portion of the probe in one or two orthogonal planes. Providing the transducer with the capability of rotation about the axis of the tip of the probe while providing the probe with the capability of articulation in at least one plane allows one to dispose the transducer in any position relative to the axis of the probe achievable using prior art four-way articulating probes, as well as a number of additional positions, and greatly simplifies the manipulative motion necessary by the surgeon to form a desired sequence of images.

The method of ultrasonic examination of a body part according to the invention includes the steps of providing a probe as above, inserting the probe through a portal so as to dispose the transducer in the vicinity of a body part to be examined, and employing control elements to independently articulate the probe and rotate the transducer, such that the transducer elements are juxtaposed to the body part to be examined, and forming an ultrasonic image thereof using generally known techniques. The method may also include the step of rotation of the transducer prior to successive imaging steps, so as to form a series of angularly-spaced images.

Other objects and aspects of the invention will become apparent from the following description thereof.

BRIEF DESCRIPTION OF THE DRAWING

The invention will be better understood if reference is made to the accompanying drawings, in which.

DESCRIPTION OF THE PREFERRED EMBODIMENTS

As indicated above, according to the invention an ultrasonic transducer at the tip of an articulated probe can be rotated about its own axis, that is, the transducer can be rotated with respect to a plane of articulation of the probe. Numerous methods for doing so are within the scope of the invention. In a first embodiment of the invention showing in detail in FIGS. 1–4 and 6–8, rotation of the transducer head to a desired angular position with respect to a plane of articulation is provided by a torque-transmitting member extending along a lumen of the probe and controlled by a control member located at a proximal end of the probe, typically as part of a handpiece also including controls for the articulation of the probe.

A second embodiment of the invention is also disclosed, providing a further method of thus rotating the transducer head with respect to the plane of articulation, so that the transducer array takes a desired orientation. It will be appreciated that in these and other possible embodiments of the invention the transducer array according to the invention is stationary with respect to the axis of the probe during the formation of each image, as distinguished from prior art systems wherein the transducer head continuously rotates in order to form an image.

In the embodiment of the probe of the invention shown in FIGS. 1–4 and 6–8, the probe 10 comprises a handpiece 12, a nonarticulated section 14, an articulated section 16, and an elongated generally cylindrical side-firing transducer head 18, comprising an array of individually actuable transducer elements 20 disposed in at least one row extending along the surface of the transducer head 18 and parallel to the axis thereof. As discussed below in connection with FIGS. 15(a)–(e), other types of transducer array are also within the scope of the invention.

The handpiece 12 comprises at least one control element 22 for controlling the articulation of the articulated section 16 of the probe. In the embodiment shown, two control elements 22 and 23 are provided for separately controlling articulation of the probe in orthogonal planes. A further control element 24 is also provided, for controlling the rotation of the transducer head 18, and thus the orientation of the transducer elements 20, with respect to the plane of articulation of the probe.

Figures 1, 5:
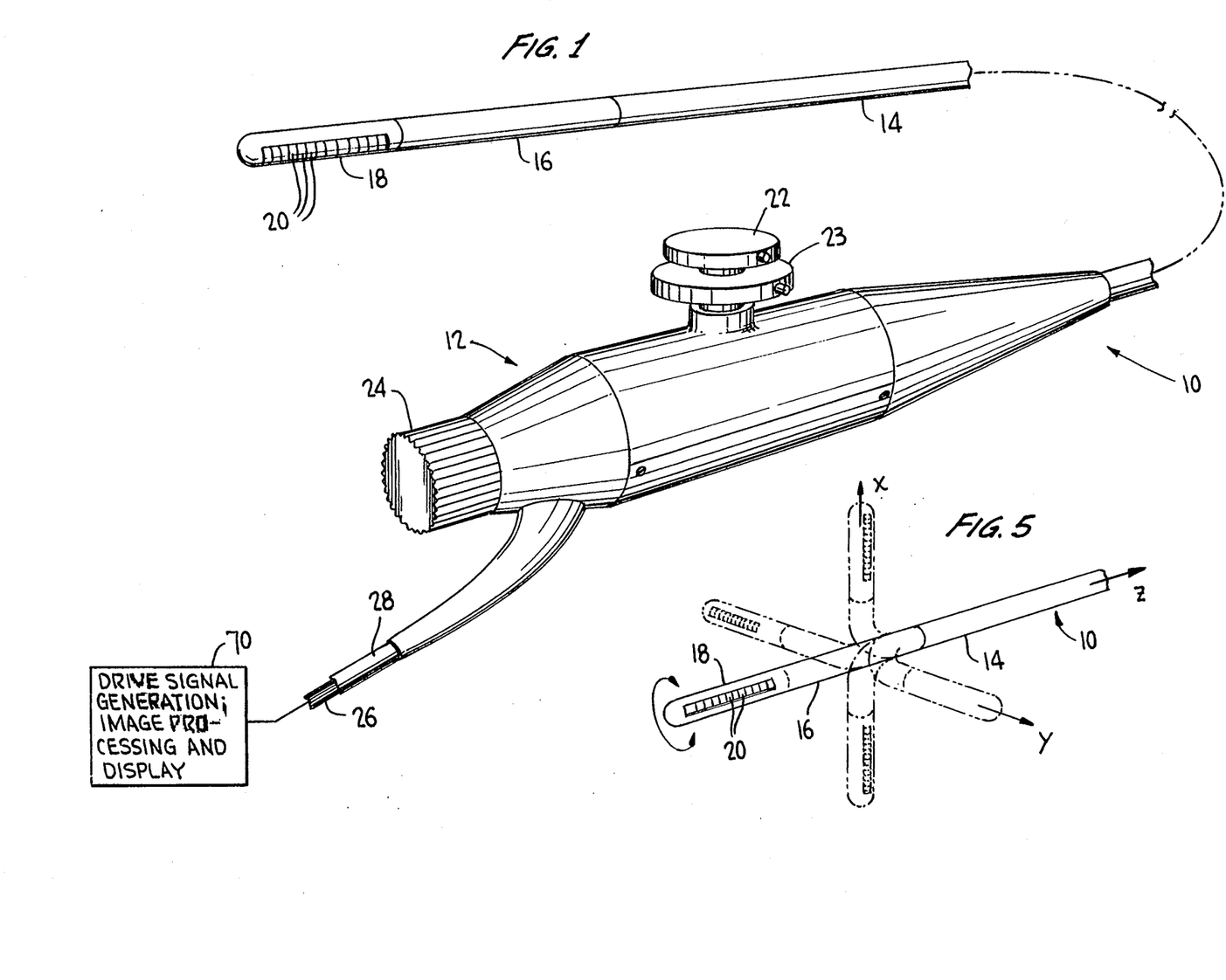
FIG. 1 shows a perspective view of an endoscope probe assembly according to the invention.
FIG. 5 illustrates various positions of the transducer head according to the invention.

FIG. 5 shows the tip of the probe 10 in a number of possible positions, according to an important aspect of the invention. The nominal straight position of the probe 10, as assumed when the articulated section 16 is not articulated in either bending plane, is shown in full; as indicated in phantom, articulable section 16 may be bent "left or right", such that the probe head lies in a horizontal plane, or may be bent "up or down" such that it lies in the orthogonal vertical plane. More specifically, if the axis of the probe is defined to include the Z axis, such that the tip of the probe lies on the Z axis when the articulable section 16 of the probe is straight, the probe can then be articulated about an axis parallel to the X axis, this being vertical in FIG. 5, so that the probe tip then lies in the Y–Z plane; alternatively, the probe can be articulated about an axis parallel to the Y axis, such that the tip lies in the X–Z plane. These motions can also be combined, such that the plane of articulation is between the X–Z and Y–Z planes.

In each case, according to an important aspect of the invention, the transducer head 18 is separately rotatable about its own axis of elongation, that is, about the axis of the tip of the probe, such that the transducer elements may be controlled to take any desired orientation with respect to the plane of articulation. This allows the transducer head to be rotated about its own axis after articulation of the probe, e.g., to form a series of angularly-spaced images; this capability is not available in the prior art.

The nonarticulated section 14 of the probe may be rigid or somewhat flexible, depending on the desired use. Typically, the nonarticulated section 14 of a probe 10 intended for insertion through a natural portal will be somewhat flexible, e.g., so as to be bendable to slide down the esophagus, while the nonarticulated section 14 of a probe intended for insertion through an artificial portal will be essentially rigid.

Returning to discussion of FIG. 1, a number of electrical conductors 26 carrying excitation signals to the transducer elements 20, and carrying signals responsive to detection of reflected ultrasonic energy from structure within a body part to be imaged, are disposed in a cable 28 extending from the handpiece 12 to "head end" equipment 70 for supplying suitable sequences of drive signals, and for storage and analysis of signals responsive to reflected energy. While conductors 26 are shown as a number of separately insulated wires, it will be understood that conductors 26 could also be provided as individual "traces" on a substrate, and might also comprise coaxial or shielded conductors. Conductors 26 run down a lumen provided in probe 10 for individual connection to transducer elements 20, as generally shown in the prior art. It should also be appreciated that the number of conductors 26 may be less than the number of individually-excitable transducer elements 20; for example, a multiplexing device may be disposed in the transducer head for connecting the excitation signals to the appropriate transducer elements 20.

Figures 2, 3, 4:
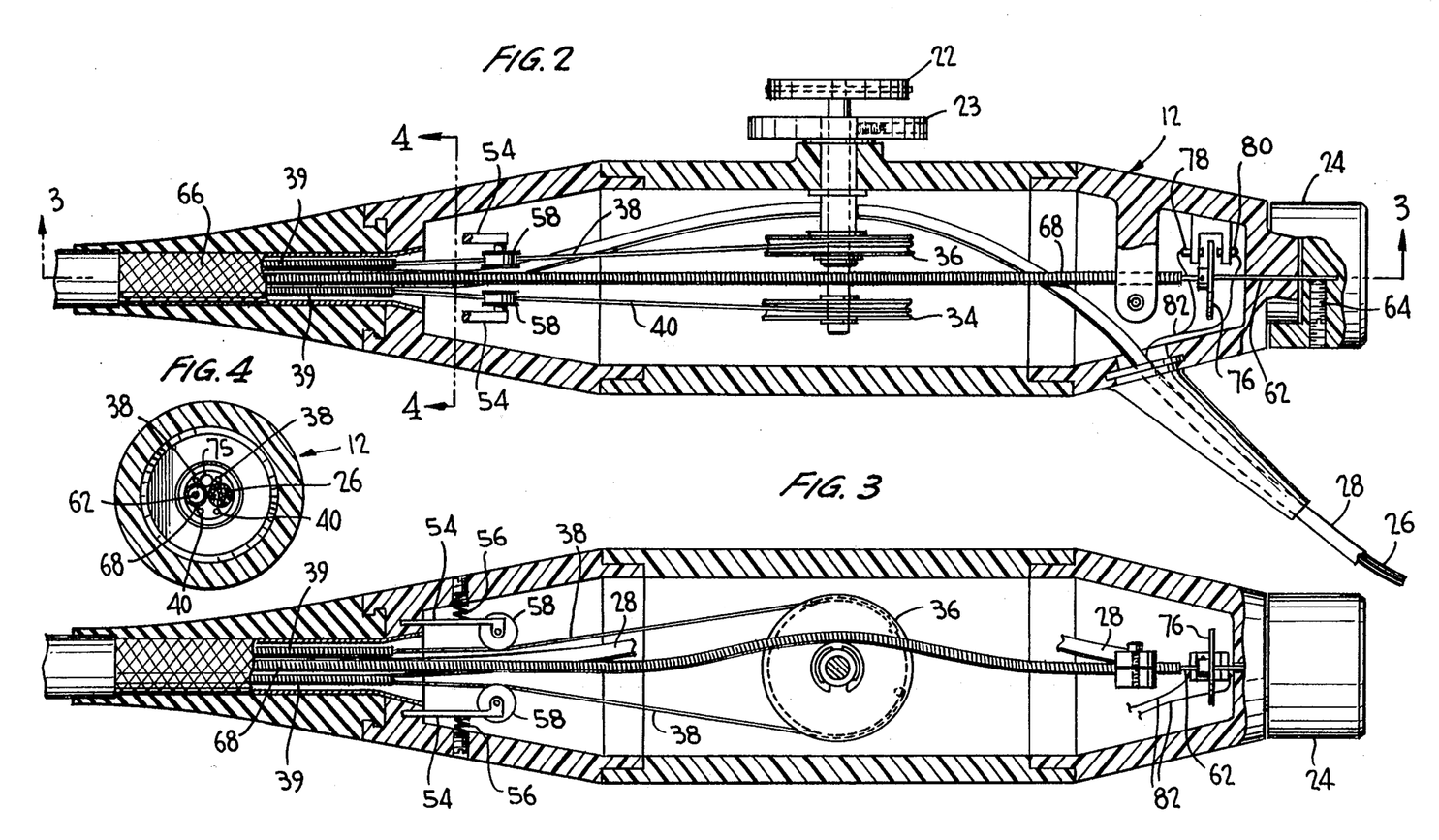
FIG. 2 shows a cross-section through the operating handpiece of the endoscope according to the invention.
FIG. 3 shows a cross-sectional view along the line 3—3 of FIG. 2.
FIG. 4 shows a cross-section along the line 4—4 of FIG. 2.

FIGS. 2, 3, and 4 illustrate typical structure provided in the handpiece 12, for controlling articulation of the articulated section 16 of the probe 14 about orthogonal axes, and for rotation of the transducer head 18 about the axis of the tip of the probe so as to control the orientation of the transducer elements 20 with respect to the plane of articulation. Coaxial control knobs 22 and 23 control articulation of the probe by permitting rotation of capstans 34 and 36, respectively. Capstans 34 and 36 control tension on two pairs of tension members 40 and 38, respectively. Capstans 34 and 36, together with control knobs 22 and 23, comprise a push-pull control arrangement for the pairs of tension members 38 and 40, i.e., upon rotation of control knob 23, capstan 36 is rotated, releasing tension on one of the members of pair of tension members 38, while exerting tension on the other.

Figures 6, 8:
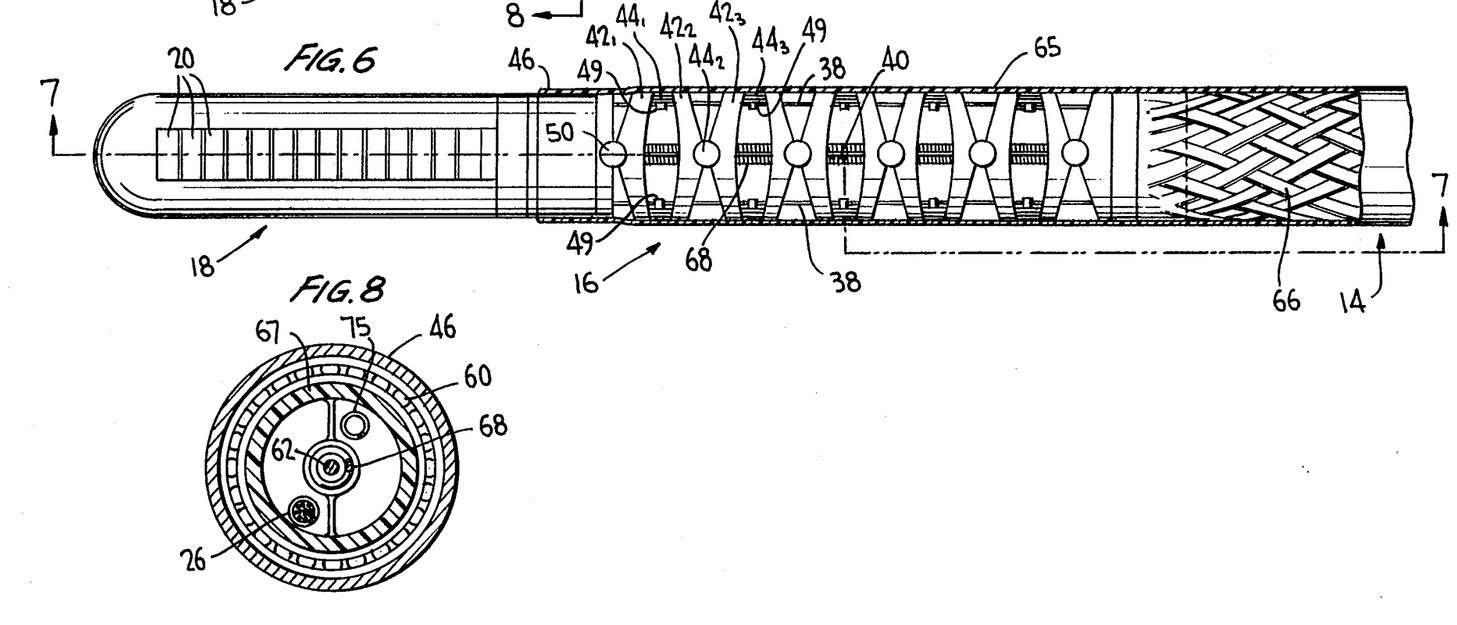
FIG. 6 shows a partially cut-away view of the tip of the probe according to the invention.
FIG. 8 shows a cross-sectional view along line 8—8 of FIG. 7.
Figure 7:
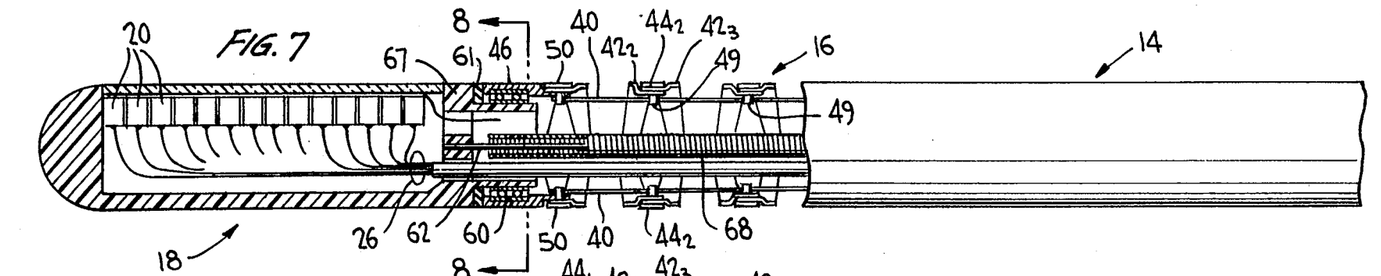
FIG. 7 shows a partial cross-sectional view along line 7—7 of FIG. 6.

Referring to FIGS. 6 and 7, the articulated section of the probe 16 comprises a number of substantially identical vertebrae $42_1$, $42_2$, $42_3$, . . . . Vertebrae $42_1$, $42_2$, $42_3$ . . . are pivoted to one another by pairs $44_1$, $44_2$, $44_3$ . . . of pivot members (typically rivets) defining orthogonal axes about which alternating pairs of vertebrae 42 are pivoted. For example, the distal vertebra $42_1$ is pivoted by a pair 50 of pivot members to a proximal member 46 of the probe head assembly 18, that is, pair 50 defines a pivot axis extending out of the plane of FIG. 6, and in the plane of FIG. 7. Vertebra $42_1$ is pivoted at $44_1$ to the next vertebra $42_2$, that is, about a pivot axis extending through pair $44_1$ of pivot members, in the plane of FIG. 6. Vertebra $42_2$ is pivoted to the next vertebra $42_3$ about an axis extending out of the plane of FIG. 6, defined by pair $44_2$ of pivot members, and so on.

The pairs of tension members 38 and 40 are affixed to the distal member 46 of the articulated section 16 of the probe, and run through bearings 49 formed on pairs $44_1$, $44_2$, $44_3$ . . . of pivot members. Accordingly, when tension is exerted on one of the members of the pair 38 of tension members, e.g., the lower member in FIG. 6, this pulls vertebrae $42_1$, $42_2$, $42_3$ . . . together along that tension member. Simultaneously, tension is released on the upper member of pair of tension members 38, such that the articulated section 16 bends downwardly, in the plane of FIG. 6. If tension had been applied to one of the other pair 40 of tension members, and released from the other, the articulated section 16 of probe 10 would correspondingly bend up or down with respect to the plane of FIG. 6, in the plane of FIG. 7.

As shown in FIGS. 2 and 3, pivoted tension control members 54 are spring biased at 56 to exert tension on tension members 38 and 40 via rollers 58, so as to remove any slack from the operating mechanism.

According to an important aspect of the invention, transducer head 18 is rotatable about the axis of the tip of the probe 10 such that the transducer elements 20 can take any desired orientation with respect to the plane of articulation, enabling the transducer elements 20 to be juxtaposed as desired to a body structure to be examined. In the embodiment of FIGS. 1–4 and 6–8, the transducer head is made rotatable with respect to the probe by mounting in a bearing 60 at the distal tip of the articulated portion 16 of the probe 10. The probe head 18 is supported by a member 67 mounted on the inner race of bearing 62. See FIG. 8. A torque transmitting member 62 is fixed to member 67 and runs thence down the lumen of the probe to reach control knob 24 fixed thereto by a set screw 64. Accordingly, when control knob 24 is rotated, torque transmitting member 62 rotates likewise, rotating the transducer head 18 about the axis of the distal tip of the probe 10, independent of any articulation of the probe.

As noted above, "four-way" articulable probes, as shown by the prior art, allow the transducer head to be disposed at all possible positions relative to the axis of the probe, but the actual disposition of the transducer in a desired position demands substantial manipulative skill, such that such probes are difficult to use. By providing a transducer controllably rotatable about the axis of the tip of the probe according to the invention, a two-way articulable probe is capable of providing all relative transducer locations provided in the prior art, in a substantially simplified manner, Moreover, according to the invention a series of angularly-spaced images may be made without disturbing the adjustment of the articulated section of the probe; the prior art does not provide this capability.

As noted above, the articulated section 16 of the probe permits controllable articulation of the probe in one or two planes. The nonarticulated section 14 of the probe 10 may also be somewhat flexible so as to enable the surgeon to feed the probe through a natural portal, in order to juxtapose the transducer to a body part to be examined. To this end, the nonarticulated portion 14 of the probe 10 is sheathed in a flexible braided sheath 66 as indicated in FIG. 6, and the elements running down the lumen of the probe are similarly made flexible. Accordingly, the pairs of tension transmitting members 38 and 40 are typically sheathed in flexible housings 39, the ends of which are confined at the handpiece 12 and at the distal end of the nonarticulated section 14 of the probe, so that tension may be exerted thereby despite bending of the nonarticulated section 14 of the probe. Such flexible sheaths 39 may comprise spiral wound wire elements as used for control cables in a variety of applications. The torque transmitting member 62 provided to rotate the transducer head about the axis of the tip of the probe 10 is similarly sheathed in a flexible housing 68, as conventionally used for control elements.

In order that the probe 10 can be sterilized, its outer surface is sealed; to this end, braided sheath 66 is enclosed in a flexible but impermeable tube 65, and bearing 60 is sealed. A further seal 61 may be provided between transducer head 18 and articulated section 16. A tube 75 may also be incorporated into the probe (see FIGS. 4 and 8), defining a continuous lumen for provision of biopsy or other tools at the tip of the probe.

As discussed above, electrical conductors 26 connect the transducer head 18 to external "head end" equipment 70 (FIG. 1), comprising means for supplying suitable ultrasonic drive signals to the transducer elements 20 and for processing the electrical signals provided by the transducer element responsive to reflection of the ultrasonic energy from the body structure in generally known fashion, so as to yield suitable images. Conductors 26 are similarly flexible, so that they can be routed around capstans 34 and 36 and other elements for controlling tension members 38 and 40, and so that handpiece 12 can be conveniently connected by a flexible cable 28 to the head end equipment 70.

According to a further aspect of the invention, a signal indicative of the relative angular position of the transducer head 18 about the axis of the tip of the probe may be supplied to the head end equipment 70 analyzing the signals detected by the transducer elements 20 in order to provide an image. Such a signal indicative of the relative angular position of the transducer head might be used in forming a series of tomographic images. To this end, an encoder disk 76 may be mounted on the torque transmitting member 62 by which the transducer head 18 is rotated. See FIGS. 2 and 3. Typically, encoder disk 76 is a transparent member with opaque radial lines disposed between a light source 78 and a detector 80, such that the signals from the detector 80 are indicative of rotation of the disk 76 therebetween. Such signals can accordingly be supplied to the head end equipment 70 by further conductors 82.

Figure 9:
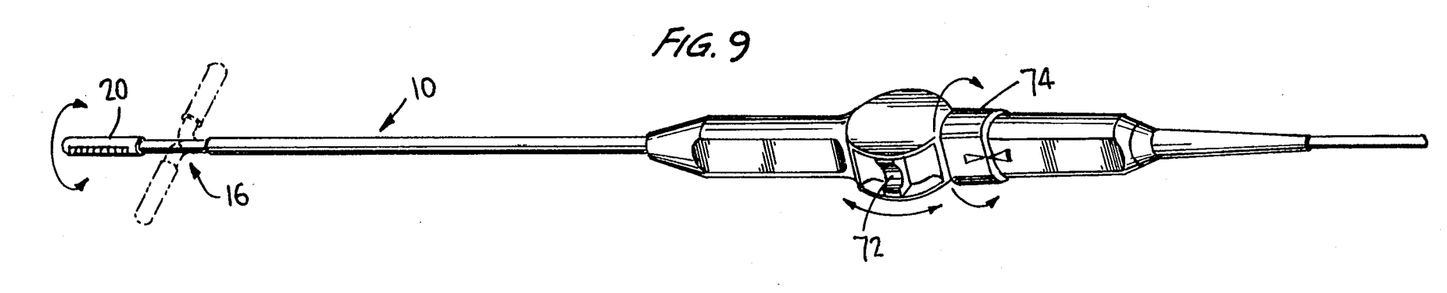
FIGS. 9–11 show various alternative configurations for the probe according to the invention, the probe itself being generally similar in each of these embodiments, while the handpiece configuration varies.
Figure 10:
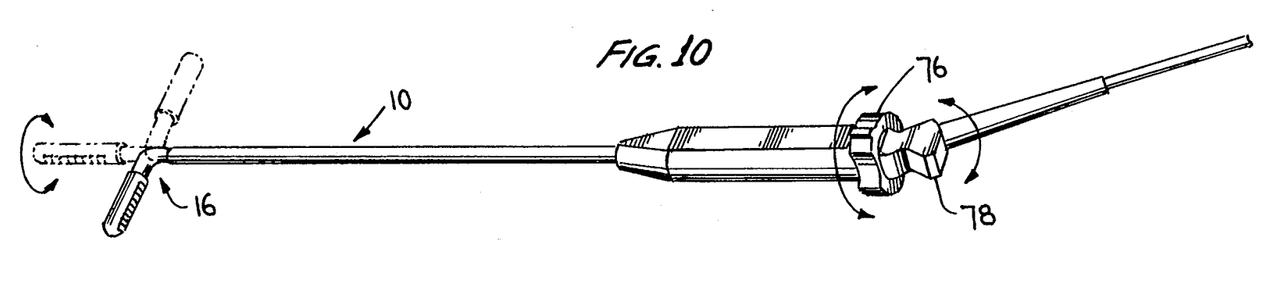
Figure 11:
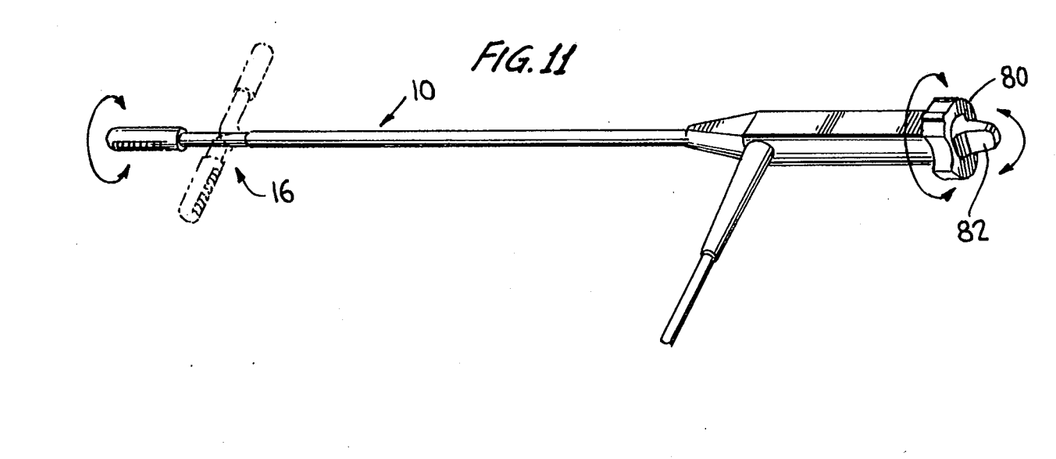

FIGS. 9, 10, and 11 show additional possible embodiments of this invention. In each case, the probe 10 is generally similar. For example, in the embodiment of FIG. 9 a two-way articulated section 16 is provided, controlled by a rocker member 72 moving in the direction indicated by the arrows. The rotation of the transducer head 20 about the axis of the tip of the probe is controlled by a rotatable control element 74, as shown. Similarly, in FIG. 10 the rotation of the probe head 20 is controlled by a rotatable control member 76, while the pivoting of the articulated section of the probe 16 is controlled by a lever element 78. Still further, the rotation of the probe head 20 in the embodiment of FIG. 11 is controlled by a rotatable member 80 and the pivoting of the articulated section 16 by a toggle member 82.

Figure 12:
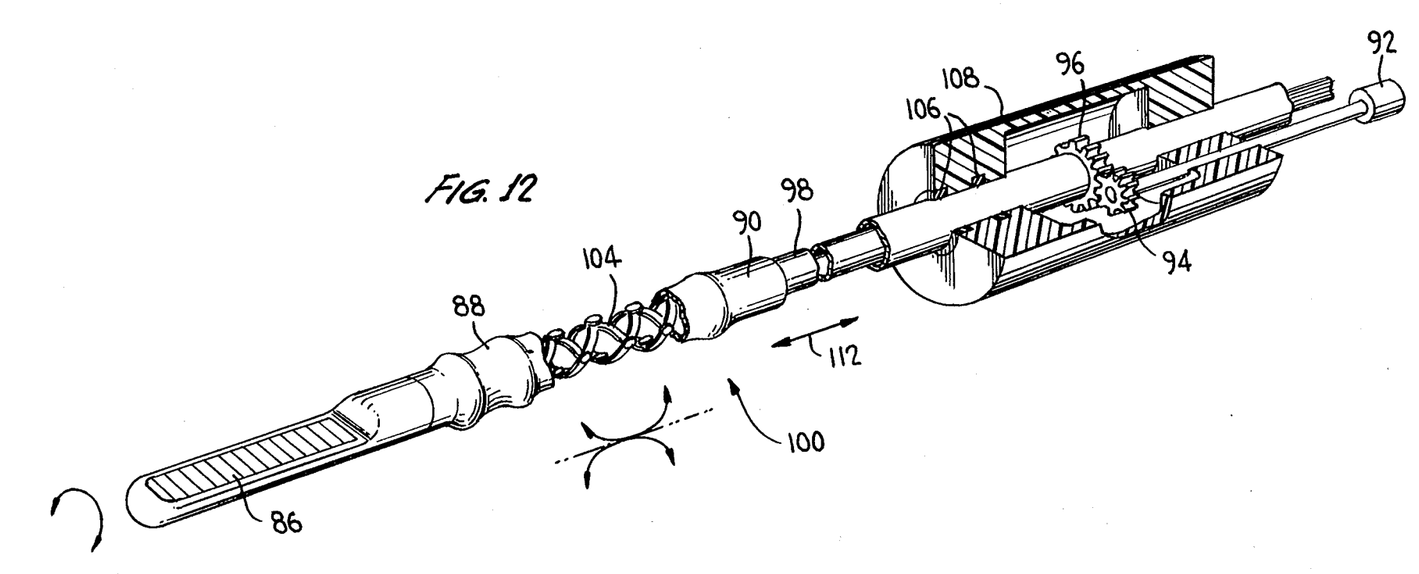
FIG. 12 shows a partially cut-away perspective view of a further embodiment of the articulated ultrasonic probe according to the invention.
Figure 13:
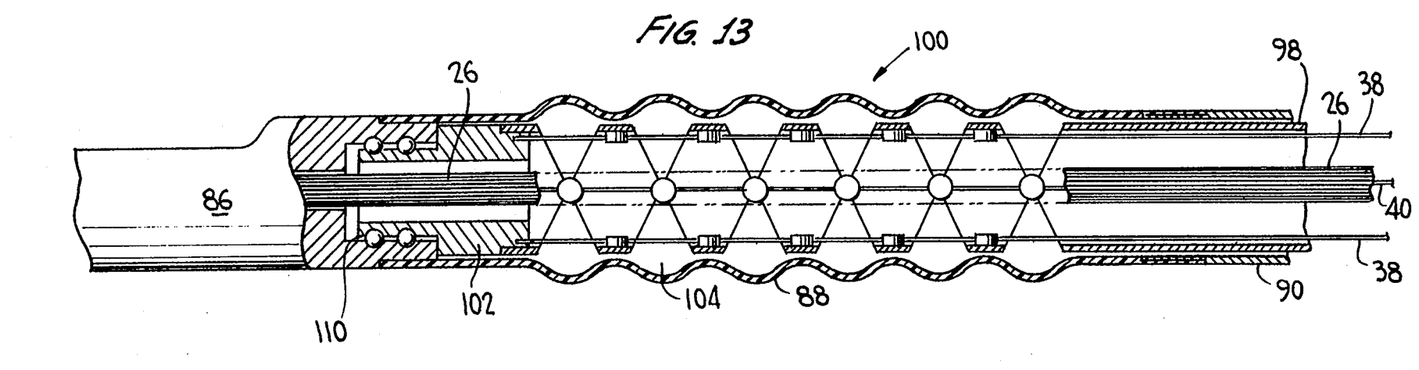
FIG. 13 shows a cross-sectional view through the articulated section of the probe of FIG. 12.

FIGS. 12 and 13 show a further embodiment of the invention. In the embodiment discussed in detail above in connection with FIGS. 1–4 and 6–8, the transducer head is rotated about the axis of the tip of the probe by a torque-transmitting member running down the lumen of the probe. By comparison, in the embodiment shown in FIGS. 12 and 13, the transducer head 86 is rotated by a flexible bellows 88 in turn connected to an outer substantially rigid tube 90 rotatable with respect to a coaxial inner tube 98. The outer tube 90 may conveniently be rotated by a control knob 92 geared by spur gears 94 and 96 to the outer tube 90. Rotation of the outer tube 90 rotates the bellows 88 and hence the probe head 86 with respect to the stationary inner tube 98. The probe again includes an articulated section 100, in this embodiment comprising an articulating mechanism 104 fixed to the stationary inner tube 98 and enclosed within bellows 88. Accordingly, as outer tube 90, bellows 88 and transducer head 86 rotate, the orientation of the transducer varies with respect to the plane of articulation defined by the articulated mechanism 104. The structure of the articulated mechanism 104, and its control, are generally as described above.

As shown in the cross-sectional view of FIG. 13, the transducer head 86 is journaled by bearings 110 to the distal end of nonrotating articulated mechanism 104, within bellows 88. As the mechanism 104 is operated to articulate the probe, the bellows 88 allows articulation of the outer rotatable portion of the probe, such that the transducer head 86 can be rotated with respect to the plane of articulation of the probe. Accordingly, bellows 88, transducer head 86 and outer tube 90 all rotate around inner tube 98 and articulated mechanism 104, together with the electrical conductors 26 and tension members 38 and 40 used to control the articulation of the articulated section 100. As indicated by arrow 112, the outer tube may be spring-biased axially inwardly in order to straighten the bellows 88 as needed.

The embodiment of the invention shown in FIGS. 12 and 13 has the advantage that because the elements making up the outer surface of the probe rotate as one, the probe head need not be connected to the articulated section by a sealed bearing in order to prevent leakage during sterilization or use of the probe of the invention. The bellows should be formed of a flexible material that is durable throughout a number of flexures, so as to avoid leakage; polyethylene is one possible material choice. The outer tube 90 is sealed to the handpiece 108 of the probe by seals 106, allowing relative rotation thereof. The entire probe assembly may be immersed for sterilization or disinfection, as needed. If cable 28 is terminated by a cable connector for connection to external circuitry as at 70, the cable connector may be sealed during the sterilization operation according to the invention of copending Ser. No. 08/152,135 filed Nov. 16, 1993.

It will be appreciated that the improved endoscopic ultrasonic probe according to the invention allows substantial flexibility in endoscopic imaging of body structures. Endoscopic imaging according to the method of the invention typically involves the steps of inserting the probe into a surgical portal such that the probe is disposed generally in the vicinity of a structure to be examined, and manipulating one or more control elements operating the articulated section of the probe, and a further control element controlling the rotation of the ultrasonic transducer about the axis of the tip of the probe, so as to juxtapose the transducer to the structure to be examined. Suitable drive signals are then supplied to the transducer elements such that ultrasonic energy is transmitted into the structure to be examined. The transducer elements detect reflection of ultrasonic energy from structures within the body part to be examined, and provide signals responsive thereto. These signals travel back up the conductors of the connecting cable 28 for analysis and generation of images generally in accordance with the teachings of the prior art. Typically, the image is a cross-section corresponding to an image plane I defined by one or a sequence of beams of ultrasonic energy extending into the body part to be imaged; the image plane I includes the axis of elongation of the transducer.

Figure 14A:
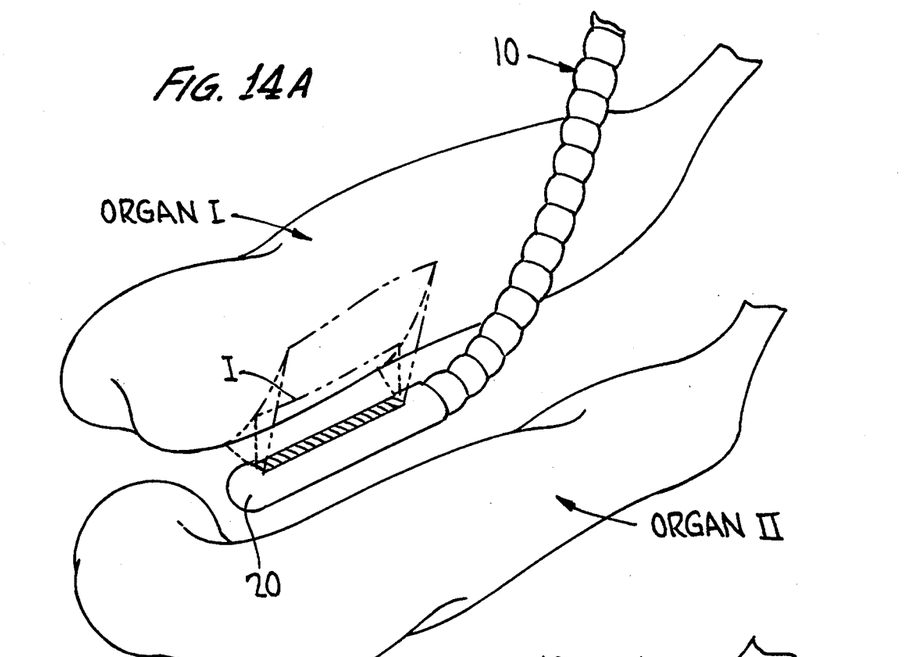
FIGS. 14(a) and (b) show diagrammatically the formation of a plurality of angularly-spaced images as made possible according to the invention.
Figure 14B:
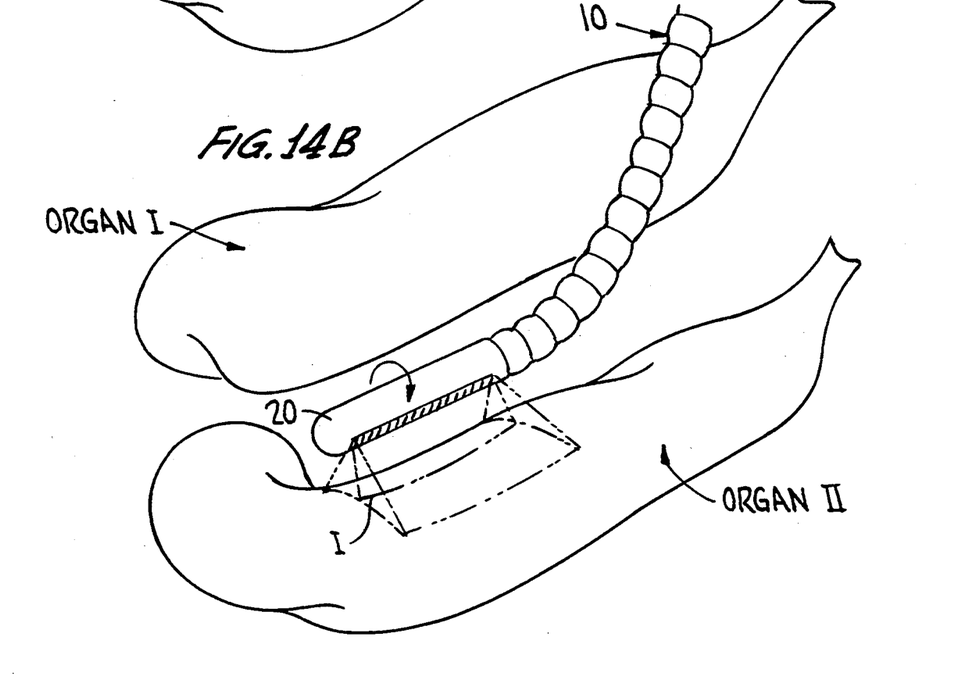

According to the invention, the same process can be repeated after rotation of the transducer through a small angle, e.g., by rotating control knob 24; the result is a series of angularly-spaced cross-sectional images. As shown by comparison of FIGS. 14(a) and (b), such a series of angularly-spaced images, amounting to cross-sections in a sequence of image planes I, taken about the axis of the tip of probe 10, can be formed according to the invention by rotation of the transducer 20, even after articulation of the probe 10 so as to juxtapose the transducer to the body structure to be imaged. This facility is not available in the prior art. The facility of rotation of the transducer with respect to the axis of the tip of the probe may further be employed to allow the transducer to follow closely along complex organ contours for generation of a succession of images or the like.

Figure 15:
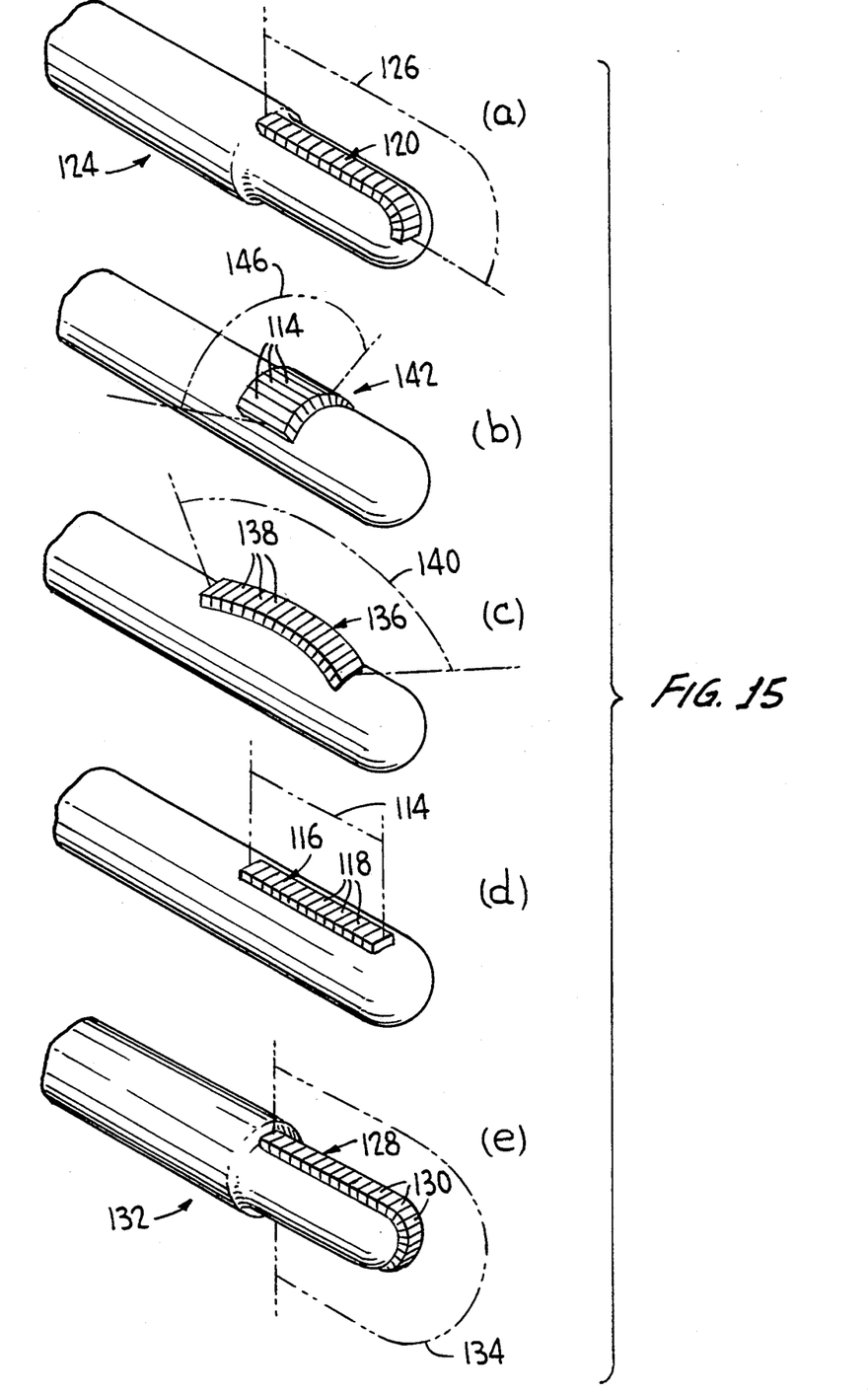
FIG. 15 provide examples of various transducer head assemblies useful in connection with the invention.

As discussed above, the invention can be implemented employing numerous differing transducer array designs, the choice being made depending on the precise nature of the image to be formed. FIGS. 15(a)–(e) provide examples of such transducer array designs. FIG. 15(d) shows an elongated array 116 of tranducer elements 118 extending longitudinally along the tip of the transducer, as shown in the other Figures; this transducer emits ultrasonic energy in a generally rectangular beam 114, imaging structure in a planar region including the axis of the transducer tip.

As examples of other transducer designs within the scope of the invention, the transducer of FIG. 15(a) includes an elongated array 120 of transducer elements 122 extending around the tip of the probe 124, such that structure is imaged in a plane 126 lying to one side and extending around the end of the probe. The transducer array 128 of FIG. 15(e) is similar, but the elements 130 are disposed symmetrically around the tip of the probe 132. Accordingly, structure is imaged in a generally semicircular region 134. The beams 126 and 134 both lie in a plane including the axis of the tip of the probe. The transducer array of FIG. 15(c) is comparable to that of FIG. 15(d), except that the elements 138 of the FIG. 15(c) array 136 are arranged in an arcuate pattern, such that a fan-shaped beam 140 is emitted, again in a plane including the axis of the tip of the probe. Finally, the transducer array 142 of FIG. 15(b) includes elements 144 arranged in an arcuate pattern extending around the probe; in this case, the axis of the probe is perpendicular to the plane of the beam emitted, which images structure in a fan-shaped region transverse to the tip of the probe.

As indicated, each of these and further transducer array designs are within the scope of the invention, and may be usefully employed in connection with the probe of the invention. Further, various known methods of exciting the elements of the transducer arrays are similarly within the invention; these include so-called phased-array and beam steering techniques. Other known transducer designs, including arrangements wherein a single element is mechanically scanned to transmit a beam into a sequence of angularly- or linearly spaced regions, are likewise considered to be within the scope of the invention.

It will be apparent that there are numerous additional embodiments and features of the invention, and of instruments implementing the invention, that can be provided. For example, articulation of the probe and rotation of the transducer head using electric motors to control either or both of these motions is within the scope of the invention. It is also within the scope of the invention to provide locking devices for securing the articulated probe and rotatable transducer head in their respective positions when a desired position has been attained.

Therefore, while a preferred embodiment of the invention has been described the invention should not be limited thereby, but only by the following claims.

What is claimed is:

1. An ultrasonic probe assembly, comprising:
  a generally cylindrical elongated transducer head, adapted to be placed in a stationary position against a body part to be ultrasonically examined, and comprising a transducer array comprising a plurality of transducer elements individually excitable to emit ultrasonic energy in a predetermined pattern;

an elongated probe, said probe including a controllably-articulable section disposed near the distal end of said probe, the axes of elongation of said transducer head and of said probe being substantially coaxial when said articulable section is straight;

first control means at a proximal end of said probe for controlling articulation of said articulable section of said probe in at least one plane of articulation;

said transducer head being mounted to a distal end of said articulable section of said probe by means permitting rotation of said transducer head about its axis of elongation;

second control means at a proximal end of said probe for controlling rotation of said transducer head about its axis of elongation, such that the relative circumferential position of said transducer array with respect to said plane of articulation may be controlled; and electrical conductor means extending along the length of said probe for carrying excitation signals and detected signals between said proximal end of said probe and said transducer head.

2. The ultrasonic probe assembly of claim 1, wherein said articulable section of said probe comprises a series of vertebrae spaced along said articulable section of said probe and pivotally connected to one another, such that said vertebrae can be drawn toward one another along a first line extending longitudinally substantially along the outer surface of the probe while being spread apart from one another along a second line diametrically opposite to said first line, thus articulating said probe to bend in a plane of articulation including said lines.

3. The ultrasonic probe assembly of claim 2, wherein said assembly further comprises two tension members arranged opposite one another and extending parallel to said first and second lines, and wherein said first control means at a proximal end of said probe for controlling articulation of said articulable section of said probe in at least one plane comprises push-pull control means for controllably exerting tension on one said tension member while controllably releasing tension on the opposite tension member, thus controlling articulation of said articulable section of said probe in said plane.

4. The ultrasonic probe assembly of claim 2, wherein said vertebrae are pivotally connected to one another by means permitting alternating pairs of said vertebrae to pivot with respect to one another about orthogonal pivot axes, and wherein said assembly comprises two pairs of tension members spaced substantially equally about the outer circumference of said probe and connected between the distal end of said articulable portion of said probe and said first control means at the proximal end of said probe, said pairs of tension members being arranged pair-wise for push-pull control of the tension exerted thereby responsive to said first control means, such that said articulated section of said probe is separately controllable for articulation in orthogonal planes.

5. The ultrasonic probe assembly of claim 1, wherein said separately excitable elements of said transducer array are arranged to transmit a pattern of one or more beams of ultrasonic energy into a structure to be examined, said pattern lying generally in a plane including the axis of elongation of the tip of said probe.

6. The ultrasonic probe assembly of claim 1, wherein said transducer head is journaled to said articulable section of said probe, said assembly further comprising a flexible torque-transmitting member extending along a central lumen extending the length of said probe, said torque-transmitting member being fixed at a distal end to said transducer head and to said second control means at its proximal end, for controlling rotation of said transducer head about the axis of elongation of said probe.

7. The ultrasonic probe assembly of claim 1, further comprising position sensing means operatively attached to said transducer head for providing a signal responsive to the relative angular position thereof.

8. The ultrasonic probe assembly of claim 1, wherein a nonarticulated section of said probe comprises coaxial tubular members, an outer one of said members being joined to said transducer head by a flexible bellows enclosing an articulating mechanism of said probe, whereby said outer tubular member, said bellows, and said transducer head may be rotated with respect to the inner of said coaxial tubular members and said articulating mechanism.

9. The ultrasonic probe assembly of claim 1, wherein said electrical conductor means extending along the length of said probe for carrying excitation signals and detected signals between said proximal end of said probe and said transducer head comprises a plurality of electrical conductors extending from the proximal end of said probe along a central lumen extending the length of said probe to said transducer head, for affecting connection of said transducer elements to means for supply of said excitation signals and means for processing said detected signals.

10. In an ultrasonic probe comprising an elongated probe having a controllably articulable section disposed near a distal end thereof, and comprising control means for controlling articulation of said probe in at least one plane of articulation including the axis of elongation of said probe, said probe further comprising an elongated transducer head comprising an array of transducer elements for emitting a pattern of ultrasonic energy, the axis of elongation of said transducer head lying substantially in said plane of articulation of said probe, and electrical conductor means extending along the length of said probe for carrying excitation signals from a source of such signals to said transducer head, and for carrying return signals responsive to detection of ultrasonic energy by said elements to means for processing said return signals, the improvement comprising:

means for mounting said transducer head for rotation about its axis of elongation, and control element means connected to a flexible torque-transmitting member arranged for controllably rotating said transducer head about its axis of elongation, such that said array may be disposed at substantially any desired orientation with respect to the plane of articulation of said articulable section of said probe in response to manipulation by hand of such control element means.

11. The improvement of claim 10, wherein said flexible torque-transmitting member is disposed in a lumen extending the length of said probe and connected at its distal end to said transducer head for rotating said transducer head, said control element being connected to the proximal end of said torque-transmitting member for controllable rotation thereof.

12. The improvement of claim 11, wherein said control element is a finger-grippable knob for ready application of torque to said torque-transmitting member.

13. The improvement of claim 10, wherein a nonarticulated section of said probe comprises coaxial members, an outer one of said members being joined to said transducer head by a flexible bellows enclosing an articulating mechanism of said probe, whereby said outer members, said bellows, and said transducer head may be rotated with respect to the inner of said coaxial members and said articulating mechanism.

14. A method of ultrasonic examination of a body part of a patient, comprising the steps of:
(a) providing an elongated ultrasonic probe, said probe comprising a controllably-articulable section disposed near a distal end thereof, an elongated transducer head comprising an array of individually-excitable transducer elements adapted to be disposed in in a particular position juxtaposed to a body part to be examined, said transducer head being mounted to a distal end of said articulable section of said probe for rotation about its axis of elongation, and first and second control elements for controlling articulation of said articulable section of said probe in at least a first plane, and rotation of said transducer head, respectively, whereby said transducer array may be disposed at substantially any desired orientation with respect to the plane of articulation of said probe, with the axis of elongation of said transducer head lying in said plane of articulation,
(b) inserting said probe through a portal in the body of said patient, so as to dispose said transducer head in the vicinity of a body part to be ultrasonically examined,
(c) employing said first and second control elements to independently articulate said probe and rotate said transducer, such that said elements of said array contact the body part to be ultrasonically examined in a predetermined positional relationship thereto,
(d) applying ultrasonic drive signals to each said transducer element so that each said element transmits a pattern of ultrasonic energy into the body part to be ultrasonically examined,
(e) employing each said transducer element to detect ultrasonic energy reflected from structures comprised by the body part to be ultrasonically examined,
(f) transmitting return signals responsive to said detected ultrasonic energy from each said transducer element to means for processing said signals, and
(g) processing said return signals to produce an image of the body part to be ultrasonically examined.

15. The method of claim 14, wherein said step of employing said second control element to rotate said transducer is performed by rotating a control means in turn rotating a torque-transmitting member extending the length of said probe and connected at a distal end thereof to said transducer head to rotate said transducer head.

16. The method of claim 15, wherein said control means rotating said torque-transmitting member comprises a finger-grippable knob.

17. The method of claim 14, wherein after each said transducer element has been brought into contact with the body part to be ultrasonically examined, and a first said image has been produced, said transducer is rotated about its axis and said steps (d)–(g) are reperformed, such that plural images of said body part to be examined are produced corresponding to differing relative angular positions of each said transducer element with respect to the body part to be examined.

18. The method of claim 17, comprising the further step of generating an angular position signal responsive to the relative angular position of said transducer head, and employing said angular position signal to identify the relative angular position of said transducer during performance of said step (g) of processing said return signals to produce an image.

19. An ultrasonic probe assembly, comprising:
an elongated probe, said probe including a controllably-articulable section disposed near the distal end of said probe;
a generally cylindrical elongated transducer head comprising a transducer excitable to emit ultrasonic energy in a predetermined pattern defining an image plane, adapted to be placed in a stationary position against a body part to be ultrasonically examined;
said transducer head being mounted to a distal end of said articulable section of said probe by means permitting rotation of said transducer head about its axis of elongation, such that the axes of elongation of said transducer head and of said probe are substantially coaxial when said articulable section is straight;
first control means at a proximal end of said probe for controlling articulation of said articulable section of said probe in at least one plane of articulation;
second control means at a proximal end of said probe for controlling rotation of said transducer head about its axis of elongation, such that the relative circumferential position of said image plane with respect to said plane of articulation may be controlled in order to ultrasonically examine structure of interest; and
electrical conductor means extending along the length of said probe for carrying excitation signals and detected signals between said proximal end of said probe and said transducer head.

20. The ultrasonic probe assembly of claim 19, wherein the axis of elongation of the transducer head lies substantially in said image plane.

* * * * *